United States Patent [19]
Jarl

[11] Patent Number: 5,795,165
[45] Date of Patent: Aug. 18, 1998

[54] ELECTRODE CONNECTOR JACK FOR AN IMPLANTABLE MEDICAL ELECTRICAL STIMULATOR

[75] Inventor: Per Jarl, Järfälla, Sweden

[73] Assignee: Pacesetter AB, Solna, Sweden

[21] Appl. No.: 657,327

[22] Filed: Jun. 3, 1996

[30] Foreign Application Priority Data

Jun. 6, 1995 [SE] Sweden ................................. 9502057

[51] Int. Cl.⁶ .................................................. H01R 4/58
[52] U.S. Cl. ............................................................. 439/86
[58] Field of Search ........................ 439/86, 593, 669; 128/419, 419 R, 419 P, 419 S, 607, 608, 639; 607/36, 37, 38

[56] References Cited

U.S. PATENT DOCUMENTS

| | | |
|---|---|---|
| 3,721,869 | 3/1973 | Paoli ..................................... 439/86 X |
| 3,920,172 | 11/1975 | Rhee ..................................... 439/86 X |
| 4,898,173 | 2/1990 | Daglow et al. . |
| 4,909,751 | 3/1990 | Marolda, Jr. . |
| 4,934,366 | 6/1990 | Truex et al. . |
| 4,934,367 | 6/1990 | Daglow et al. ..................... 439/86 X |
| 5,012,807 | 5/1991 | Stutz, Jr. . |
| 5,358,409 | 10/1994 | Obara . |

*Primary Examiner*—J. J. Swann
*Assistant Examiner*—Daniel Wittels
*Attorney, Agent, or Firm*—Hill & Simpson

[57] ABSTRACT

An electrical connector jack has at least one disk-shaped element made of an elastic, conductive material which has one or more contact surfaces arranged to come into contact with the corresponding contact surfaces on a contact pin. A layer of insulating, elastic material is provided on both sides of the electrically conductive material. The disk-shaped element is elastically deformed by the contact pin when the pin is inserted into the connector jack, so the contact surfaces of the electrically conductive material and the insulating material are pressed against the corresponding contact surfaces on the contact pin, the contact surfaces being protectively sealed by the contact surfaces of the insulating material.

16 Claims, 2 Drawing Sheets

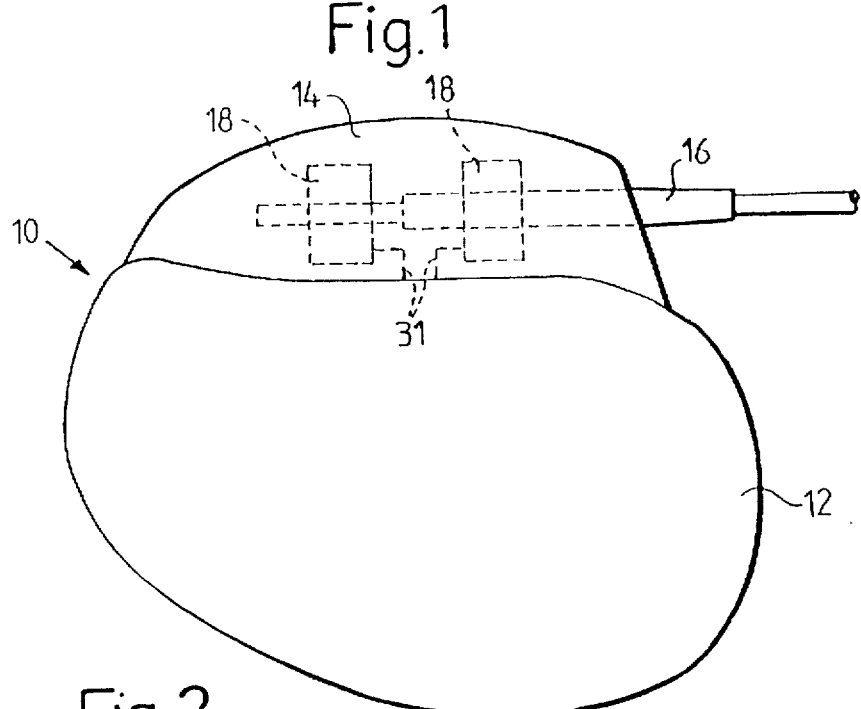
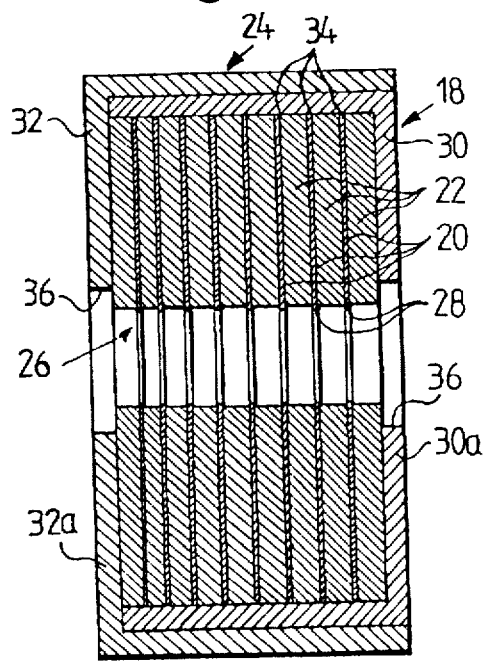
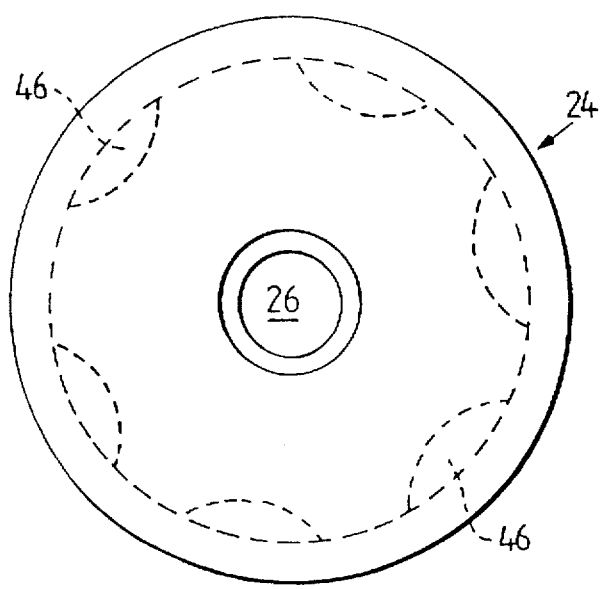

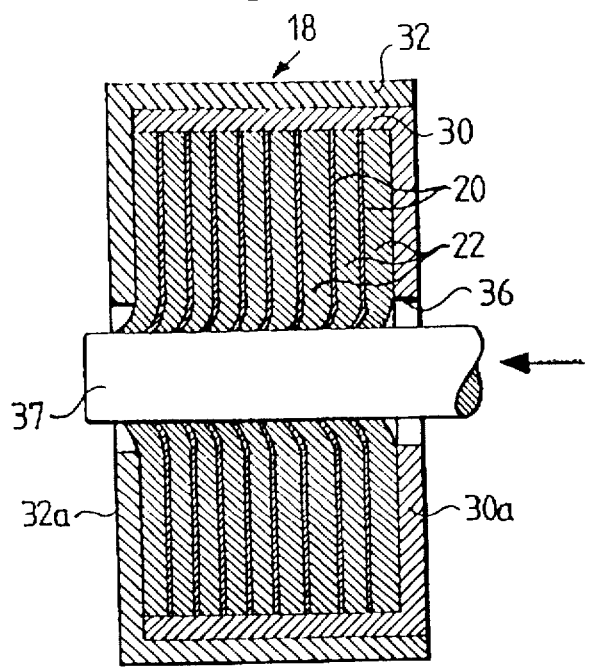
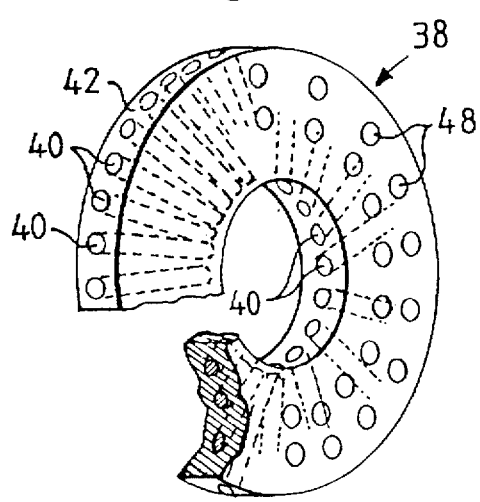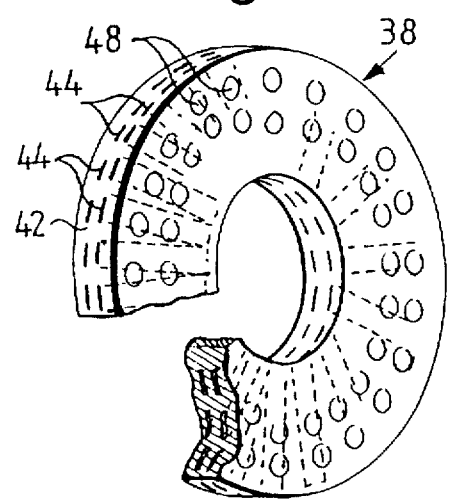

ELECTRODE CONNECTOR JACK FOR AN IMPLANTABLE MEDICAL ELECTRICAL STIMULATOR

BACKGROUND OF THE INVENTION

1. Field of the Invention

The present invention relates to an electrical connector jack, particularly for contact with a contact pin on the proximal end of an electrode cable, connectable to an implantable heart stimulator, such as a pacemaker or defibrillator.

2. Description of the Prior Art

Connectors of the above type are intended for installation in a connection section of the heart stimulator for electrical connection of a contact surface on the proximal end of the electrode cable, which is insertable into the connection part of the generating electronics of the heart stimulator section.

A common connector for this purpose has a metal shell into which the contact pin of the electrode cable is inserted and affixed with a locking screw accessible from outside the connection section. The locking screw achieves contact between the shell and the pin at the same time as the electrode cable is axially locked in place, keeping the electrode cable from detaching from the connection section. These screws require manual action to achieve contact.

Connectors for this purpose have been proposed which make possible automatic, forced contact between the contact pin and connector jack when the electrode pin in inserted into the connector jack. For example, U.S. Pat. No. 4,934, 366 and 5 012 807 describe such a connector jack, made from a ring-shaped element, which, when the pin is inserted, is axially compressed against a corresponding contact on the pin, thereby achieving mechanical contact on all sides between the male contact pin on the electrode and the connector jack in the heart stimulators contact section. The contact sites are sealed with separate sealing means arranged on the exterior of the contact pin end of the electrode cable and/or on the interior of the connector jack.

European Application 0 339 877 also discloses a connector jack for a pacemaker which contains electrically conductive elastomer rings making possible both forced mechanical coupling and electrical contact between contact surfaces, as well as simultaneous sealing against fluid leakage at the contact pin. Such contact rings have no well-defined contact and sealing areas, so these electrically conductive, elastic rings must be supplemented with separate sealing rings to achieve effective sealing of the contact surfaces.

SUMMARY OF THE INVENTION

An object of the present invention is to provide an improved, electrical connector jack of the type initially described wherein discreet, resilient, electrically conductive means are pressed against the contact pin's contact surfaces to achieve simultaneous, protective sealing of distinct contact surfaces with an electrically insulating material to prevent junction corrosion at the contact sites and the leakage of fluid past the contact surfaces.

The above object is achieved according to the invention in a connector having at least one disk-shaped element, containing electrically conductive material, with one or more contact surfaces arranged to come into contact with the corresponding contact 10 surfaces on the contact pin, as well as a layer of insulating, elastic material on both sides of the electrically conductive material, at least in the area of the contact surfaces interacting with the contact pin. The disk-shaped element is arranged to be elastically deformed by the contact pin when the pin is inserted into the connector jack, so the electrically conductive material's contact surfaces and the insulating material are pressed against the corresponding contact surfaces of the contact pin while contact surfaces are protectively sealed by the insulating material at the same time.

In a preferred embodiment of the invention, the connector contains two or more disk-shaped multilayered assemblies, made of electrically conductive material, with intermediate coatings of elastic insulating material and an external coating of elastic, insulating material. The assembly has a recess, matching the peripheral configuration of the contact pin, the contact surfaces of the multilayered assembly being formed by the inner end edges of the multilayered assembly exposed in the recess. The assembly is arranged to deform elastically when the contact pin is inserted into the recess, pressing the contact surfaces of the multi layer assembly against the contact pin's corresponding contact surfaces while the contact surfaces are protectively sealed by the insulating material at the same time.

According to an alternative embodiment of the invention, the connector has one or more disks made of an elastic, electrically insulating material, one or more layers made of electrically conductive material, primarily on the plane of the disk, being embedded in each insulating disk. Each disk has a recess, matching the contact pin's peripheral configuration, with the inner end edges of the layers exposed in the recess forming contact surfaces arranged to press against the contact pin's corresponding contact surfaces when the contact pin is inserted into the recess of the disk or disks, with, simultaneous protective sealing of the contact surfaces by the elastic insulating material.

DESCRIPTION OF THE DRAWINGS

FIG. 1 is a lateral view of a pacemaker with a schematically shown connector for sealed contact with the corresponding contact pin surfaces on a bipolar electrode cable constructed in accordance with the principles of the present invention.

FIG. 2 is a schematic, axial, longitudinal, sectional view of a connector jack according to a first embodiment of the invention.

FIG. 3 is an end view of the connector in FIG. 2.

FIG. 4 is a view, corresponding to FIG. 2, but showing the deformation of the electrically conductive element and the sealing around the contact surfaces against a contact pin, inserted into the connector, on the proximal end of the electrode cable.

FIG. 5 is a perspective view of an alternative embodiment of a connector jack according to the invention.

FIG. 6 is a view, like FIG. 5, of a further embodiment of the invention.

DESCRIPTION OF THE PREFERRED EMBODIMENTS

FIG. 1 schematically depicts a pacemaker 10 with an electronics section 12 and a connection section 14 for a bipolar electrode cable 16. Two connector jacks 18 according to the invention are mounted onto or molded into the connection section 14, each jack receiving a polar contact surface on the proximal end of the electrode cable 16 which is insertable into and affixable in the connection section 14.

As FIG. 2 shows, each connector 18 can contain a plurality of electrically conductive lamellae 20 which are kept separated by elastic, electrically insulating disks 22 made of e.g. silicone. The disks 20 and 22 are preferably laminated together into a cohesive multilayer "sandwich" which can be kept in place by a surrounding housing 24 made of an electrically conductive material. The electrically conductive multilayered disks 20 and insulation disks 22 in the multi layer "sandwich" have a central hole 26 whose diameter is somewhat smaller than the external diameter of the electrode contact surface which is to be brought into contact with the multi layer disks 20 for a purpose to be described in greater detail below. The inner edge surfaces 28 of the multi layer disks 20 are exposed in the hole 26 and can be displaced radially somewhat from the inner periphery 22 of the insulating disks in order to create distinct contact surfaces inside the connector jack 18.

The shell 24 consists of two U-shaped housing halves 30 and 32, one half telescoping into the other, whereby the inner housing half 30 can be force-fitted into the outer half 32 during simultaneous clamping of the multi layer "sandwich".

The radial, external contact surfaces 34 of the conductive lamellae 20 are, like the inner edge areas 28, exposed so they can distinctly contact the conductive housing half 30, which by means of conductors 31 shown in FIG. 1, connect the connector jack to the electronics unit 12. The bottom sections 30a and 32a of the housing halves 30 and 32, which form the end walls of the connector 18, have an opening 36 which is coaxial to the central hole 26 and which has a diameter somewhat greater than the diameter of the hole 26, so the multi layer "sandwich" assumes a radial, inwardly projecting configuration, in relation to the housing's openings 36, which can be easily deformed by bending, and which is deformed when a contact pin 27 on the proximal end of the electrode cable 16 is inserted into the hole 26, as shown in FIG. 4. Because the diameter of the contact pin 37 is larger than the diameter of the hole 26 in the connector jack 18, bending deformation of the radial inner edge areas of the conductive lamellae 20 occurs, causing them to be biased against the contact surface of the contact pin 37 and the opposite, internal part of the conductive housing 30 in order to enhance contact pressure between the lamellae 20, and thus also enhancing signal transmission between the electrode cable 16 and the electronics section 12.

With the proposed connector 18 according to the invention, automatic forced contact is achieved between the electrode pin 37 and the connector jack 18, as well as intimate sealing at the contact sites, due to insulating material 22, integrated into the lamellae 20, which are sealingly pressed by the said deformation against the contact pin's 37 contact surfaces, thereby preventing the development of junction corrosion at the contact surfaces and leakage of body fluid onto and past contact surfaces.

The conductive lamellae 20 can be devised in many different ways within the scope of the invention. In addition to the circular disk shape shown in FIGS. 2–4, the lamellae can have another outer, perimeter configuration. As shown in FIGS. 5 and 6, the connector jack can alternatively be made of one or more disks 38 of an elastic, insulating material. Each disk 38 has embedded therein one or more layers, primarily on the plane of the disk, made of electrically conductive material. The electrically conductive material shown in FIG. 5 is in the form of a plurality of radially arranged metal rods 40 embedded in an insulating material 42. In FIG. 6, the electrically conductive material is formed of a plurality of metal bands or strips 44, arranged in two axially separate layers and also embedded in an electrically insulating, elastic material 42, e.g. silicone. The electrically conductive material can also have another configuration appropriate to the purpose, e.g. a mesh structure not shown in the drawing.

Even in the embodiments according to FIGS. 5 and 6, the exposed radially arranged inner and outer ends of the electrically conductive means 40 and 44 are devised to press, when a contact pin is inserted, against the corresponding contact surfaces of the pin and a surrounding contact section which is connected to the electronics section 12 by a conductor, providing simultaneous, intimate sealing of the contact sites.

The multilayer "sandwich" of layers 20 and 22 and the disks 38 can be provided with recesses or holes 46 and 48 respectively to facilitate compression and deformation and, accordingly, match the shape of these parts to the electrode contact pin 37 when the pin is inserted into the connector jack.

Separate means, not shown in FIG. 1, can be arranged in the connection section 14 to keep the electrode cable 16 from being pulled out once contact has been established between the respective contact pin parts and the connector jack 18.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electrical connector jack for an implantable cardiac stimulator, for making an electrical connection with a contact pin at an end of an electrode cable, said electrical connector jack comprising:

at least one disc shaped means, having a longitudinally extending opening adapted to receive a contact pin, containing a planar layer of electrically conductive material having a contact surface disposed in said opening for making electrical contact with said contact pin, said disc-shaped means having planar layers of insulating, elastic material respectively disposed on opposite sides of and parallel to said layer of electrically conductive material and at least in a region of said contact surface, said layers of insulating elastic material and said layer of electrically conductive material being collectively elastically deformed radially and longitudinally by said contact pin as long as said contact pin is inserted into said opening for producing a continuous surface of the electrically conductive material and the insulating material pressing against said contact pin for making an electrical connection with said contact pin while simultaneously protectively sealing said contact surface of said electrically conductive material.

2. An electrical connector jack as claimed in claim 1 wherein said disc-shaped means comprise a plurality of disc-shaped layers of electrically conductive material, alternating with an external coating of electrically insulating material, each disc-shaped layer of electrically conductive material having a recess and said disc-shaped means having a plurality of electrical contact surfaces, respectively formed by respective inner edges of said plurality of disc-shaped layers of electrically conductive material at said recess of each disc-shaped layer.

3. An electrical connector jack as claimed in claim 2 further comprising a common conductor electrically connecting all of said disc-shaped layers of electrically conductive material.

4. An electrical connector jack as claimed in claim 3 wherein said common conductor comprises a housing of electrically conductive material containing said disc-shaped layers, said disc-shaped layers pressing against said housing and forming an electrically conductive path to said housing.

5. An electrical connector jack as claimed in claim 4 wherein said housing comprises two telescopically sliding, U-shaped shell halves, each having a bottom section pressing against the insulating layer of respective end disc-shaped layers in said disc-shaped means, and at least one of said bottom sections having ah opening therein coaxial with said openings in said disc-shaped layers for admitting said contact pin into said disc-shaped means.

6. An electrical connector jack as claimed in claim 1 wherein said disc-shaped means has a plurality of slots therein for facilitating deformation of said disc-shaped means.

7. An electrical connector jack as claimed in claim 1 wherein said insulating material comprises a plurality of notches for facilitating the formation of said disc-shaped means.

8. An electrical connector jack as claimed in claim 5 wherein each disc-shaped layer has a plurality of slots therein for facilitating deformation of said disc-shaped means.

9. An electrical connector jack for an implantable cardiac stimulator for making an electrical connection with a contact pin disposed at an end of an electrode cable, said electrical connector jack comprising:

at least one disc of elastic, electrically insulating material, said at least one disc having a longitudinally extending opening therein adapted to receive a contact pin; and a plurality of electrically conductive elements embedded in said disc, each electrically conductive element having an exposed end forming a contact surface at said opening, said contact surfaces and said electrically insulating material being collectively elastically deformed radially and longitudinally by said contact pin as long as said contact pin is inserted in said opening for producing a continuous surface of said contact surfaces and said electrically insulating material pressing against said contact pin while simultaneously protectively sealing said contact surfaces of said electrically conductive elements.

10. An electrical connector jack as claimed in claim 8 wherein said electrically conductive elements comprise a plurality of metal rods radially extending in said disc to said recess.

11. An electrical connector jack as claimed in claim 8 wherein said electrically conductive elements comprise a plurality of metal strips extending radially on said disc to said recess.

12. An electrical connector jack as claimed in claim 11 wherein said electrically conductive a housing comprises two telescopically sliding, U-shaped shell halves, each shell half having a bottom section disposed to press against an exterior of said disc, each bottom section having an opening therein coaxial with said recess and having a diameter larger than said recess for permitting elastic deformation of said disc for forcing said contact surfaces against said contact pin when said contact pin is inserted in said recess.

13. An electrical connector jack as claimed in claim 9 wherein said disc of elastic electrically conductive material has a disc plane and wherein said electrically conductive elements are embedded in said disc substantially in said disc plane.

14. An electrical connector jack as claimed in claim 8 wherein said disc has a plurality of notches therein for facilitating deformation of said disc.

15. An electrical connector jack as claimed in claim 9 further comprising a common conductor electrically connecting all of said electrically conductive elements.

16. An electrical connector jack as claimed in claim 15 wherein said common conductor comprises an electrically conductive housing in which said disc is mounted and retained, and wherein each electrically conductive element has an outer end in electrical contact with said electrically conductive housing.

\* \* \* \* \*